United States Patent
Tour et al.

(10) Patent No.: US 9,377,449 B2
(45) Date of Patent: Jun. 28, 2016

(54) NANOCOMPOSITE OIL SENSORS FOR DOWNHOLE HYDROCARBON DETECTION

(71) Applicants: James M. Tour, Bellaire, TX (US); Chih-Chau Hwang, Houston, TX (US); Wei Lu, Houston, TX (US); Gedeng Ruan, Houston, TX (US); Mason B. Tomson, Houston, TX (US); Amy Kan, Houston, TX (US); Lu Wang, Houston, TX (US); Michael S. Wong, Houston, TX (US); Gautam Kini, Houston, TX (US); George J. Hirasaki, Bellaire, TX (US); Clarence Miller, Houston, TX (US)

(72) Inventors: James M. Tour, Bellaire, TX (US); Chih-Chau Hwang, Houston, TX (US); Wei Lu, Houston, TX (US); Gedeng Ruan, Houston, TX (US); Mason B. Tomson, Houston, TX (US); Amy Kan, Houston, TX (US); Lu Wang, Houston, TX (US); Michael S. Wong, Houston, TX (US); Gautam Kini, Houston, TX (US); George J. Hirasaki, Bellaire, TX (US); Clarence Miller, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 115 days.

(21) Appl. No.: 14/387,291

(22) PCT Filed: Mar. 25, 2013

(86) PCT No.: PCT/US2013/033737
§ 371 (c)(1),
(2) Date: Sep. 23, 2014

(87) PCT Pub. No.: WO2013/142869
PCT Pub. Date: Sep. 26, 2013

(65) Prior Publication Data
US 2015/0050741 A1 Feb. 19, 2015

Related U.S. Application Data

(60) Provisional application No. 61/614,631, filed on Mar. 23, 2012.

(51) Int. Cl.
*G01N 33/24* (2006.01)
*E21B 47/10* (2012.01)

(52) U.S. Cl.
CPC .......... *G01N 33/241* (2013.01); *E21B 47/1015* (2013.01)

(58) Field of Classification Search
CPC ............................ G01N 33/24; G01N 33/241
USPC ...................... 436/25, 27–30, 139; 252/408.1
See application file for complete search history.

(56) References Cited

U.S. PATENT DOCUMENTS

| 3,751,226 A | 8/1973 | Hesse et al. |
| 3,847,548 A | 11/1974 | Keller |

(Continued)

FOREIGN PATENT DOCUMENTS

| EA | 005125 B1 | 12/2004 |
| WO | WO-0181914 A1 | 11/2001 |

(Continued)

OTHER PUBLICATIONS

International Search Report and Written Opinion for PCT/US2013/033737, mailed Jul. 25, 2013.

(Continued)

*Primary Examiner* — Arlen Soderquist
(74) *Attorney, Agent, or Firm* — Winstead PC

(57) ABSTRACT

Various embodiments of the present disclosure pertain to nanocomposites for detecting hydrocarbons in a geological structure. In some embodiments, the nanocomposites include: a core particle; a polymer associated with the core particle; a sulfur-based moiety associated with the polymer; and a releasable probe molecule associated with the core particle, where the releasable probe molecule is releasable from the core particle upon exposure to hydrocarbons. Additional embodiments of the present disclosure pertain to methods of detecting hydrocarbons in a geological structure by utilizing the nanocomposites of the present disclosure.

20 Claims, 14 Drawing Sheets

(56) References Cited

U.S. PATENT DOCUMENTS

Figure 1A:
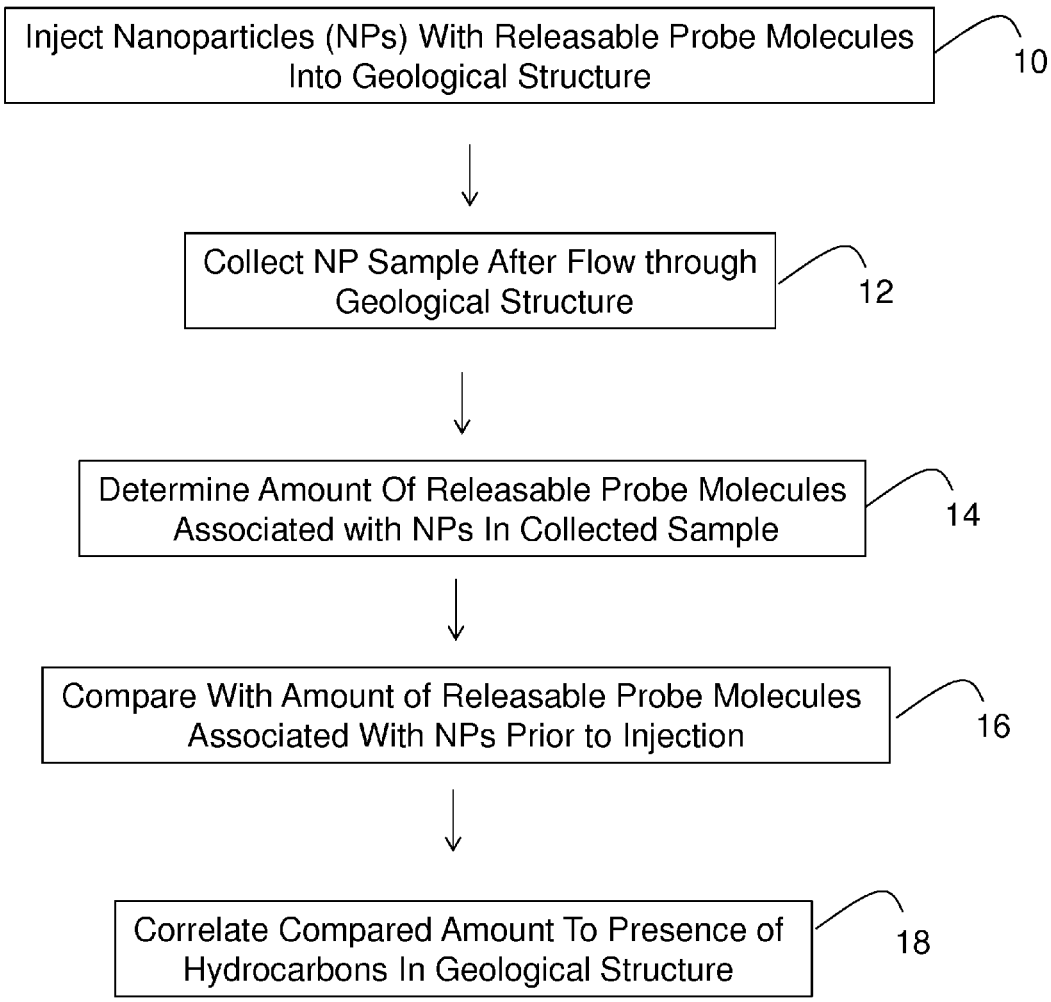

| | | | |
|---|---|---|---|
| 3,856,468 A | 12/1974 | Keller | |
| 4,770,028 A | 9/1988 | Flippo, Jr. | |
| 5,059,261 A | 10/1991 | Condo et al. | |
| 5,230,343 A | 7/1993 | Guberek et al. | |
| 5,246,860 A | 9/1993 | Hutchins et al. | |
| 5,356,465 A | 10/1994 | Eldridge | |
| 5,902,750 A | 5/1999 | Fuerholzer et al. | |
| 6,003,365 A | 12/1999 | Pope et al. | |
| 6,399,546 B1 | 6/2002 | Chang et al. | |
| 6,645,769 B2 | 11/2003 | Tayebi et al. | |
| 6,691,780 B2 | 2/2004 | Nguyen et al. | |
| 6,725,926 B2 | 4/2004 | Nguyen et al. | |
| 7,032,662 B2* | 4/2006 | Malone | E21B 47/1015 166/250.1 |
| 7,244,694 B2 | 7/2007 | Fu et al. | |
| 7,347,260 B2* | 3/2008 | Ferguson | E21B 47/1015 166/250.12 |
| 7,472,748 B2 | 1/2009 | Gdanski et al. | |
| 7,516,788 B2 | 4/2009 | Gleitman et al. | |
| 8,137,699 B2 | 3/2012 | Johnson et al. | |
| 8,313,724 B2 | 11/2012 | Hwang et al. | |
| 8,448,706 B2* | 5/2013 | Hughes | E21B 43/267 166/280.1 |
| 8,459,353 B2* | 6/2013 | Hughes | C09K 8/70 166/280.1 |
| 8,640,773 B2* | 2/2014 | Hewitt | E21B 47/1015 166/250.12 |
| 8,853,619 B2* | 10/2014 | Preudhomme | E21B 43/16 250/281 |
| 2003/0196799 A1 | 10/2003 | Nguyen et al. | |
| 2003/0196800 A1 | 10/2003 | Nguyen et al. | |
| 2004/0023479 A1 | 2/2004 | Tour et al. | |
| 2004/0067503 A1 | 4/2004 | Tan et al. | |
| 2004/0071624 A1 | 4/2004 | Tour et al. | |
| 2004/0091546 A1 | 5/2004 | Johnson et al. | |
| 2004/0094297 A1* | 5/2004 | Malone | E21B 47/1015 166/250.12 |
| 2005/0122225 A1 | 6/2005 | Kram et al. | |
| 2005/0207963 A1 | 9/2005 | Tour et al. | |
| 2006/0019408 A1 | 1/2006 | Waggoner et al. | |
| 2006/0046937 A1 | 3/2006 | Fu et al. | |
| 2006/0144588 A1* | 7/2006 | Ferguson | E21B 47/1015 166/252.6 |
| 2006/0275371 A1 | 12/2006 | Dai et al. | |
| 2007/0280876 A1 | 12/2007 | Tour et al. | |
| 2008/0063587 A1 | 3/2008 | Strano et al. | |
| 2008/0093224 A1 | 4/2008 | Tour et al. | |
| 2008/0133193 A1 | 6/2008 | Gdanski et al. | |
| 2009/0087911 A1 | 4/2009 | Ramos | |
| 2009/0215953 A1 | 8/2009 | Hwang et al. | |
| 2010/0105834 A1 | 4/2010 | Tour et al. | |
| 2010/0307745 A1 | 12/2010 | Lafitte et al. | |
| 2011/0146983 A1* | 6/2011 | Sawdon | C09K 8/36 166/276 |
| 2011/0260051 A1* | 10/2011 | Preudhomme | E21B 43/16 250/282 |
| 2012/0142111 A1 | 6/2012 | Tour et al. | |
| 2012/0171254 A1 | 7/2012 | Johnson et al. | |
| 2013/0056201 A1* | 3/2013 | Chandler, Jr. | E21B 49/02 166/254.2 |
| 2013/0087329 A1* | 4/2013 | Hewitt | E21B 47/1015 166/250.12 |
| 2013/0126158 A1 | 5/2013 | Gupta et al. | |
| 2013/0264121 A1 | 10/2013 | Young et al. | |
| 2014/0357534 A1* | 12/2014 | Barron | E21B 43/26 507/140 |

FOREIGN PATENT DOCUMENTS

| | | |
|---|---|---|
| WO | WO-2008030758 A1 | 3/2008 |
| WO | WO-2009070380 A2 | 6/2009 |
| WO | WO-2009089391 A2 | 7/2009 |
| WO | WO-2010147859 A1 | 12/2010 |
| WO | WO-2011016889 A2 | 2/2011 |

OTHER PUBLICATIONS

International Preliminary Report on Patentability for PCT/US2013/033737, mailed Oct. 2, 2014.

Berlin et al., Engineered nanoparticles for hydrocarbon detection in oil-field rocks, *Energy Environ. Sci.*, 2011,4, 505-509.

Hirasaki et al., Recent Advances in Surfactant EOR, *SPEJ*, 2011, 16, 889-907.

Wang et al., Enhanced Environmental Mobility of Carbon Nanotubes in the Presence of Humic Acid and Their Removal from Aqueous Solution, *Small*, 2008, 12, 2166-2170.

Barari et al., Synthesis and Characterization of High Molecular Weight Polyacrylamide Nanoparticles by Inverse-emulsion Polymerization, *Iran. Polym. J.*, 2011, 20, 65-76.

Chen et al, Novel gas sensor from polymer-grafted carbon black: Vapor response of electric resistance of conducting composites prepared from poly(ethylene-block-ethylene oxide)-grafted carbon black, J. Appl. Polym. Sci., 2000, 77, 2437-2447.

Shen et al., Modifying microphase separation of PVA based membranes for improving proton/methanol selectivity, Desalination, 2008, 233, 82-87.

Wang et al., Transport and Retention of Nanoscale C60 Aggregates in Water-Saturated Porous Media, Environ. Sci. Technol., 2008, 42, 3588-3594.

Li et al., Investigation of the Transport and Deposition of Fullerene (C60) Nanoparticles in Quartz Sands under Varying Flow Conditions, Environ. Sci. Technol., 2008, 42, 7174-7180.

Lecoanet et al., Laboratory Assessment of the Mobility of Nanomaterials in Porous Media, Environ. Sci. Technol., 2004, 38, 5164-5169.

Lenhart et al., Transport of Silica Colloids through Unsaturated Porous Media:? Experimental Results and Model Comparisons, Environ. Sci. Technol., 2002, 36, 769-777.

He et al., Transport of carboxymethyl cellulose stabilized iron nanoparticles in porous media: Column experiments and modeling, Colloid Interface Sci., 2009, 334, 96-102.

Saleh et al., Surface modifications enhance nanoiron transport and NAPL targeting in saturated porous media, Environ. Sci. Technol., 2007, 24, 45-57.

Lucente-Schultz, R. M., et al., Antioxidant Single-Walled Carbon Nanotubes, J. Am. Chem. Soc. 2009, 131, 3934-3941.

Liu, Zhuang, et al., Supramolecular Chemistry on Water-Soluble Carbon Nanotubes for Drug Loading and Delivery, ACS Nano 2007, 1, 50.

Green, N. M., "Avidin", 1975, Advances in Protein Chemistry, 29: 85-133 (1975).

Hwang, Chih-Chau, et al., "Highly stable carbon nanoparticles designed for downhole hydrocarbon detection", Energy Environ. Sci., 2012, 5, 8304-8309.

International Search Report for PCT/US2010/038363, filed Jun. 11, 2010, William Marsh Rice University.

Office Action for U.S. Appl. No. 13/378,440, Mailed Aug. 12, 2014.

Office Action for U.S. Appl. No. 13/378,440, Mailed Jan. 6, 2015.

Office Action for U.S. Appl. No. 13/378,440, Mailed Jul. 21, 2015.

\* cited by examiner

NANOCOMPOSITE OIL SENSORS FOR DOWNHOLE HYDROCARBON DETECTION

CROSS-REFERENCE TO RELATED APPLICATIONS

This application claims priority to U.S. Provisional Patent Application No. 61/614,631, filed on Mar. 23, 2012. This application is also related to U.S. patent application Ser. No. 13/378,440, filed on Feb. 23, 2012, which is a national stage entry of PCT/US10/38363, filed on Jun. 11, 2010, which claims priority to U.S. Provisional Patent Application No. 61/187,971, filed on Jun. 15, 2009. The entirety of each of the aforementioned applications is incorporated herein by reference.

BACKGROUND

Current sensors to detect hydrocarbons in geological structures have numerous limitations in terms of stability, durability, and breakthrough efficiency. Therefore, more effective sensors are desired for detecting hydrocarbons in geological structures.

SUMMARY

In some embodiments, the present disclosure provides nanocomposites for detecting hydrocarbons in a geological structure. In some embodiments, the nanocomposites include: a core particle; a polymer associated with the core particle; a sulfur-based moiety associated with the polymer; and a releasable probe molecule associated with the core particle, where the releasable probe molecule is releasable from the core particle upon exposure to hydrocarbons. In some embodiments, the releasable probe molecule is triheptylamine ("THA"). In some embodiments, the nanocomposites of the present disclosure have a neutral charge or a substantially neutral charge.

In some embodiments, the core particle may include at least one of carbon black, functionalized carbon black, oxidized carbon black, carboxyl functionalized carbon black, carbon nanotubes, functionalized carbon nanotubes, graphenes, graphene oxides, graphene nanoribbons, graphene oxide nanoribbons, metal nanoparticles, silica nanoparticles, silicon nanoparticles, silicon oxide nanoparticles, silicon nanoparticles bearing a surface oxide, and combinations thereof.

In some embodiments, the releasable probe molecule is non-covalently associated with the core particle.

In some embodiments, the polymer is covalently associated with the core particle. In some embodiments, the polymer may include at least one of poly(vinyl alcohol) ("PVA"), poly(ethylene glycol) ("PEG"), poly(propylene glycol) ("PPG"), poly(ethylene imine) ("PEI"), sorbitol, polysaccharides, polylactone, polyacrylonitrile ("PAN"), polyethylene ("PE"), poly(vinyl chloride) ("PVC"), poly(acrylic acid) ("PAA"), polystyrene ("PS"), high impact polystyrene ("HIPS"), polypropylene ("PP"), polyester, poly(hydroxyalkyl ester), poly(butadiene) vinyl polymers, condensation polymers, and combinations thereof. In some embodiments, the polymer is poly(vinyl alcohol) ("PVA").

In some embodiments, the sulfur-based moiety is covalently associated with the polymer. In some embodiments, the sulfur-based moiety is a sulfate moiety with the following chemical formula: —$OSO_3R$, where R is one of H, Na, K, Li, $NH_4$, alkyl groups, aryl groups, phenyl groups, and combinations thereof. In some embodiments, the sulfur-based moiety is a sulfonate moiety with the following chemical formula: —$SO_3R$, where R is one of H, Na, K, Li, $NH_4$, alkyl groups, aryl groups, phenyl groups, and combinations thereof. In some embodiments, the sulfur content of the nanocomposites of the present disclosure is less than about 2 atomic %.

In some embodiments, the present disclosure pertains to systems and methods for detecting hydrocarbons in a geological structure by utilizing the nanocomposites of the present disclosure. In some embodiments, the systems and methods include: injecting the nanocomposites into the geological structure; collecting a sample of the nanocomposites after flow through the geological structure; determining the amount of the releasable probe molecules associated with the nanocomposites in the collected sample; comparing the determined amount with the amount of releasable probe molecules associated with the nanocomposites prior to injection into the geological structure; and correlating the compared amount to presence of hydrocarbons in the geological structure. In some embodiments, the releasable probe molecule is triheptylamine ("THA"). In some embodiments, a decrease in the amount of releasable probe molecules associated with nanocomposites in the collected sample is indicative of the presence of hydrocarbons in the geological structure.

BRIEF DESCRIPTION OF THE FIGS.

Figure 1B:
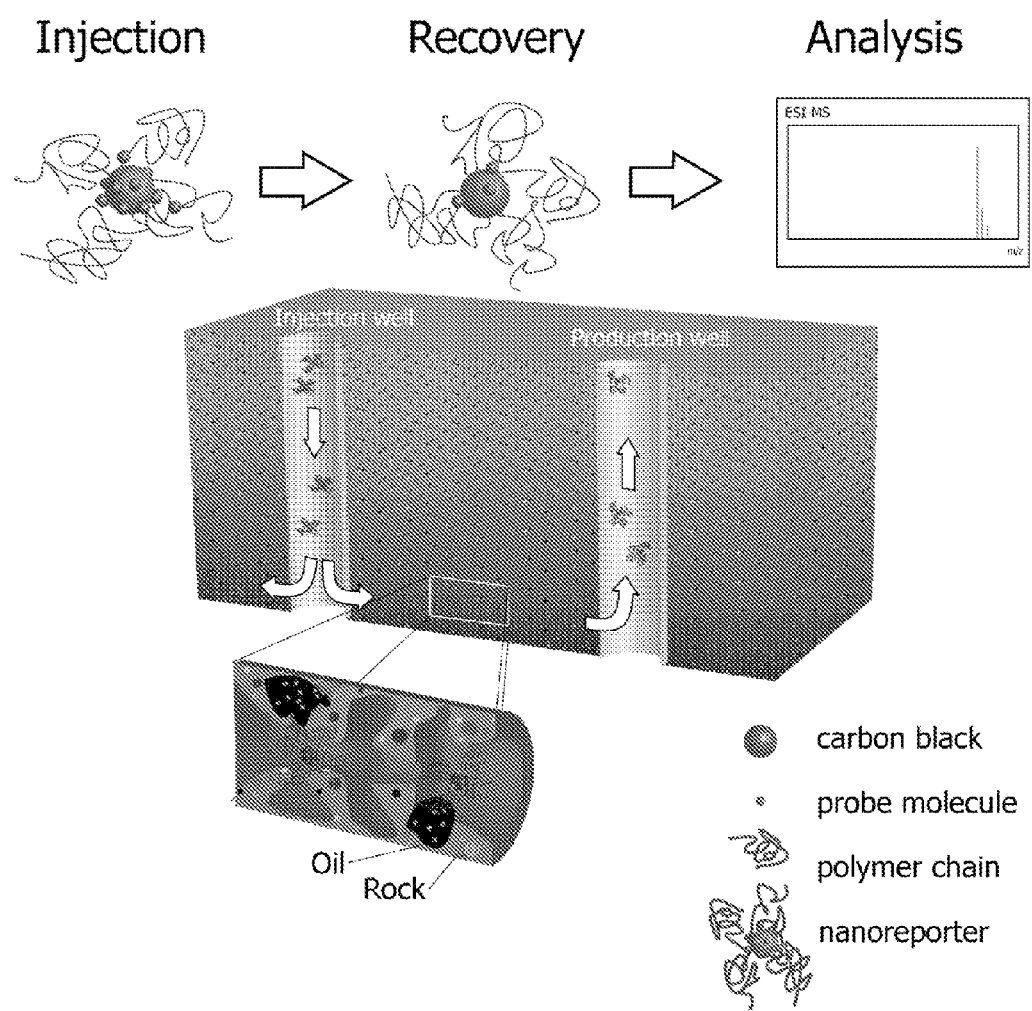

FIG. 1 provides a scheme (FIG. 1A) and a diagram (FIG. 1B) of systems and methods for detecting hydrocarbons in a geological structure through the use of nanocomposites.

Figure 2:
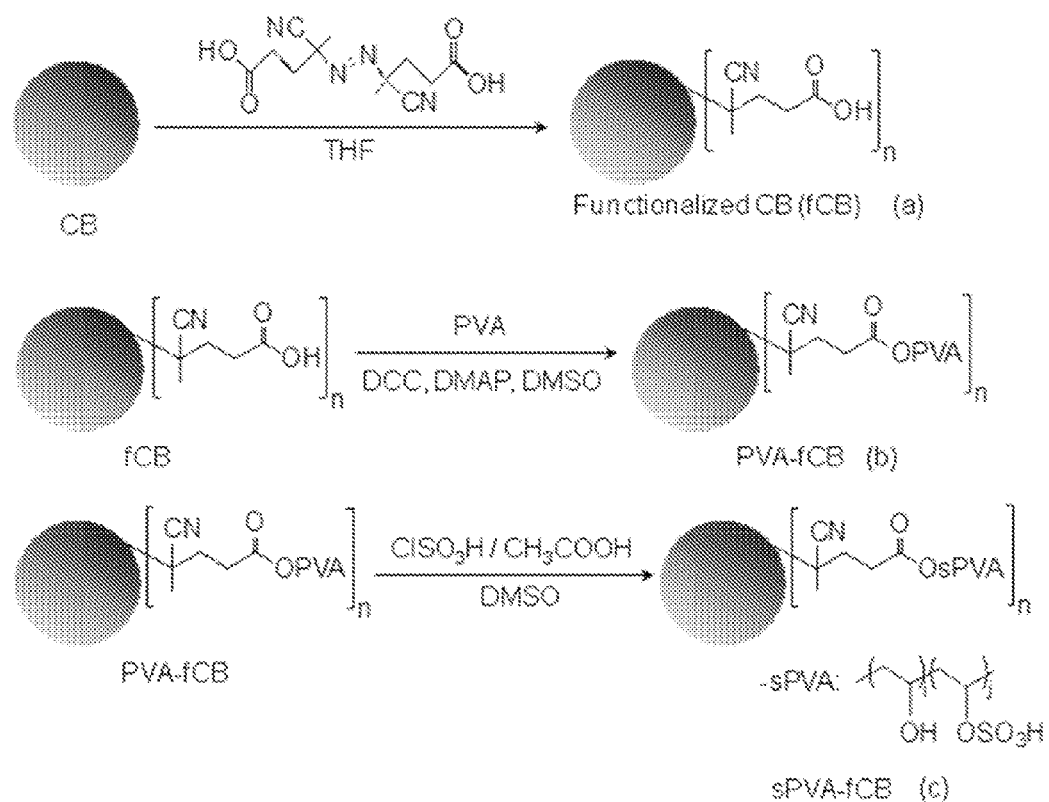

FIG. 2 provides schemes for the synthesis of various nanocomposites for hydrocarbon detection in geological structures, including functionalized carbon black ("fCB") (FIG. 2A); polyvinyl alcohol-modified fCB ("PVA-fCB") (FIG. 2B) and sulfated PVA-fCB ("sPVA-fCB") (FIG. 2C). Sulfation yields units with —$OSO_3H$ pendants. The particle size of the carbon black may be ~15 nm.

Figure 3:
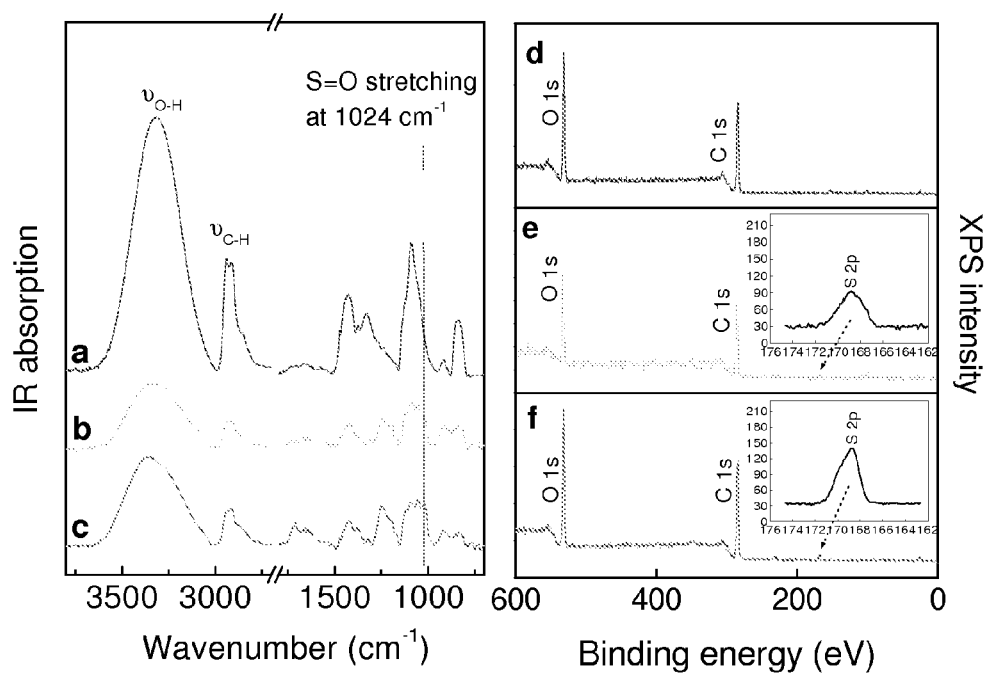

FIG. 3 provides spectral analyses of various nanocomposites, including attenuated total reflection infrared ("ATR-IR") spectrum of PVA(50k)-fCB (FIG. 3A); ATR-IR spectrum of low sulfated PVA(50k)-fCB ("LsPVA(50k)-fCB") (FIG. 3B); ATR-IR spectrum of high sulfated PVA(50k)-fCB ("HsPVA(50k)-fCB") (FIG. 3C); X-ray photoelectron spectroscopy ("XPS") spectrum of the PVA(50k)-fCB (FIG. 3D); XPS spectrum of the LsPVA(50k)-fCB (FIG. 3E); and XPS spectrum of the HsPVA(50k)-fCB (FIG. 3F). The insets in FIGS. 3E-3F are the high resolution S2p XPS spectra of LsPVA(50k)-fCB and HsPVA(50k)-fCB nanocomposites, respectively. All XPS peaks were normalized with respect to the C=C peak at 284.8 eV.

Figure 4:
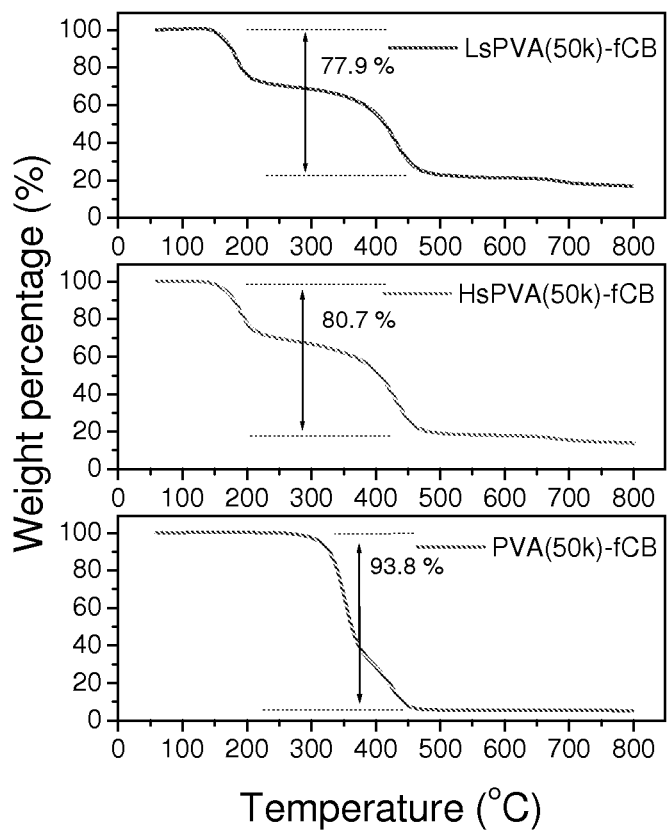

FIG. 4 provides thermogravimetric analysis ("TGA") of LsPVA(50k)-fCB, HsPVA(50k)-fCB and PVA(50k)-fCB. Samples were pretreated at 120° C. for dehydration prior to being heated to 800° C. at a rate of 3° C./minute in Ar.

Figure 5:
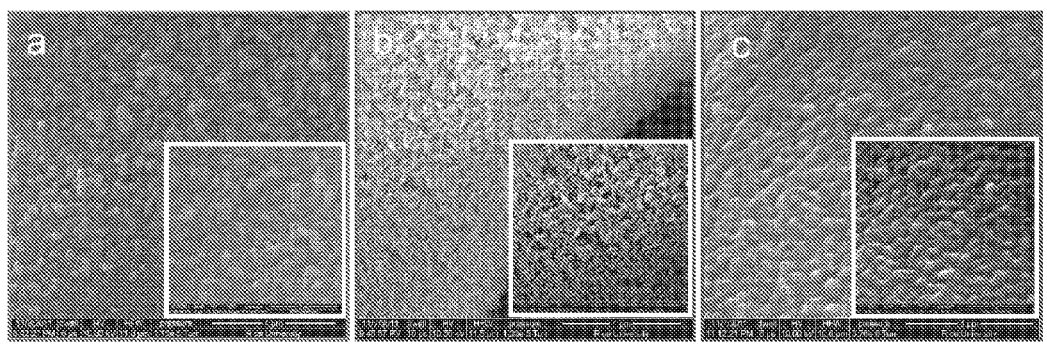

FIG. 5 provides scanning electron micrograph ("SEM") images and enlarged insets of PVA(50k)-fCB (FIG. 5A); LsPVA(50k)-fCB (FIG. 5B); and HsPVA(50k)-fCB (FIG. 5C). The scale bar for each main image is 4 µm and 2 µm for each inset.

Figure 6:
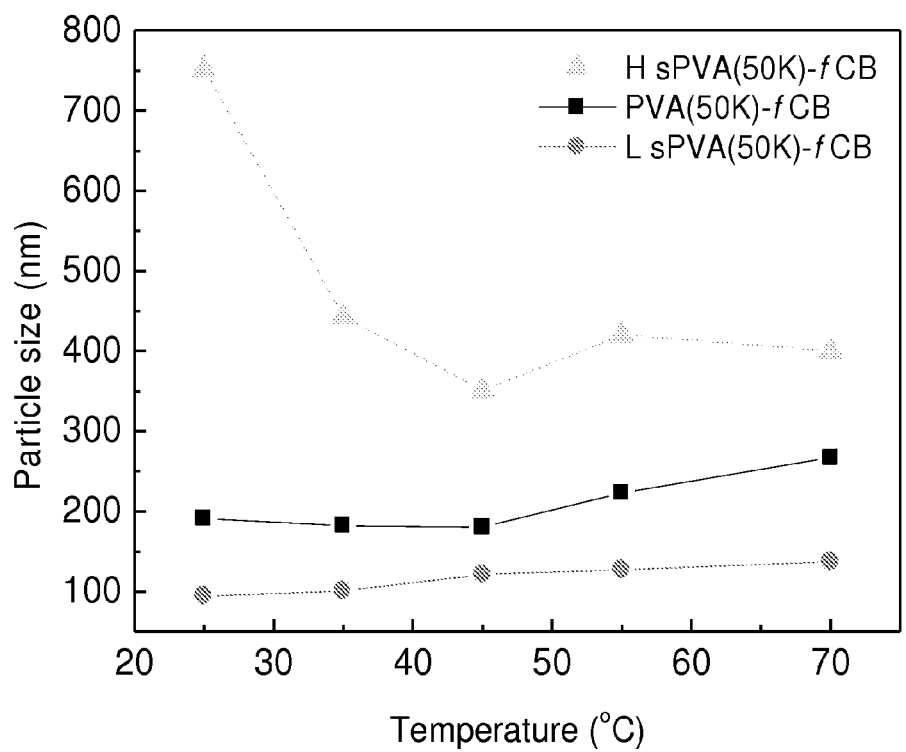

FIG. 6 provides dynamic light scattering ("DLS") plots for the PVA(50k)-coated fCB nanocomposites before and after the treatment with light or high sulfation. All nanocomposites were dispersed in deionized water. The temperature was controlled from 25° C. to 70° C.

Figure 7:
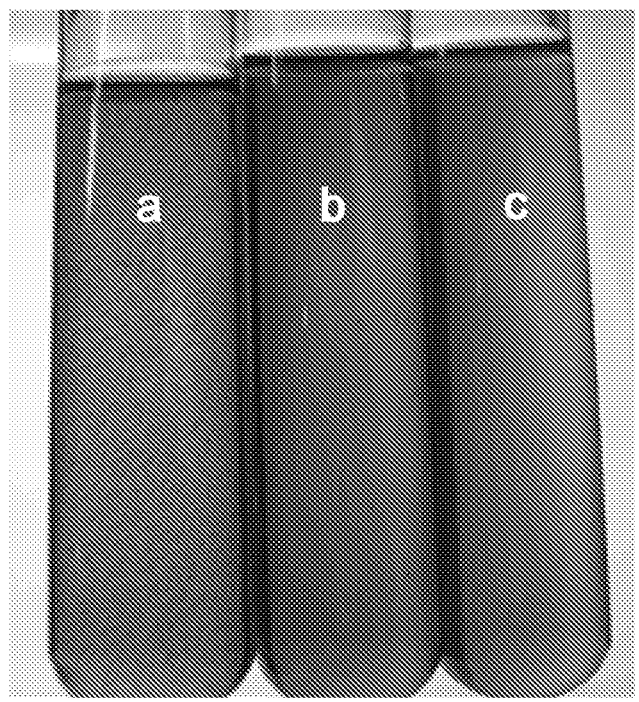

FIG. 7 provides photographs taken of the PVA(50k)-fCB (FIG. 7A); LsPVA(50k)-fCB (FIG. 7B); and HsPVA(50k)-fCB (FIG. 7C) at 100° C. All nanocomposites were suspended in API standard brine solution. The API standard brine solution was composed of 90% $H_2O$, 8% NaCl, and 2% $CaCl_2$.

Figure 8:
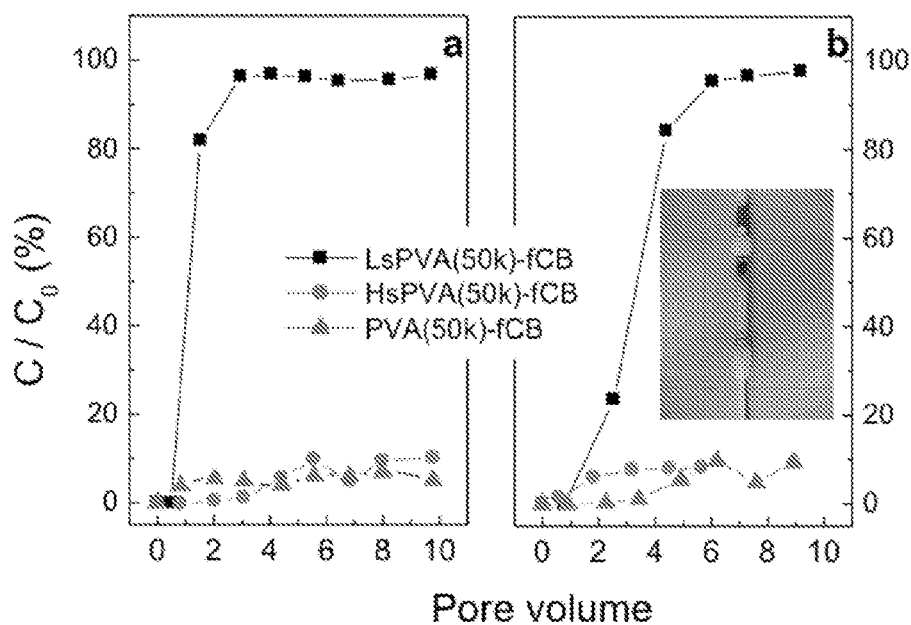

FIG. 8 provides breakthrough tests for PVA(50k)-fCBs, LsPVA(50k)-fCBs and HsPVA(50k)-fCBs in sandstone (FIG. 8A) and calcite-packed columns at 70° C. (FIG. 8B). API standard brine solution was used as aqueous carrier solution, and nanocomposites were injected into column at a flow rate of 8 mL/hour and a linear velocity of 9.3 m/24 hours. The inset in FIG. 8B shows that the HsPVA(50k)-fCBs block the column (black band at the top of the column), resulting in little breakthrough after ~6 PV.

Figure 9:
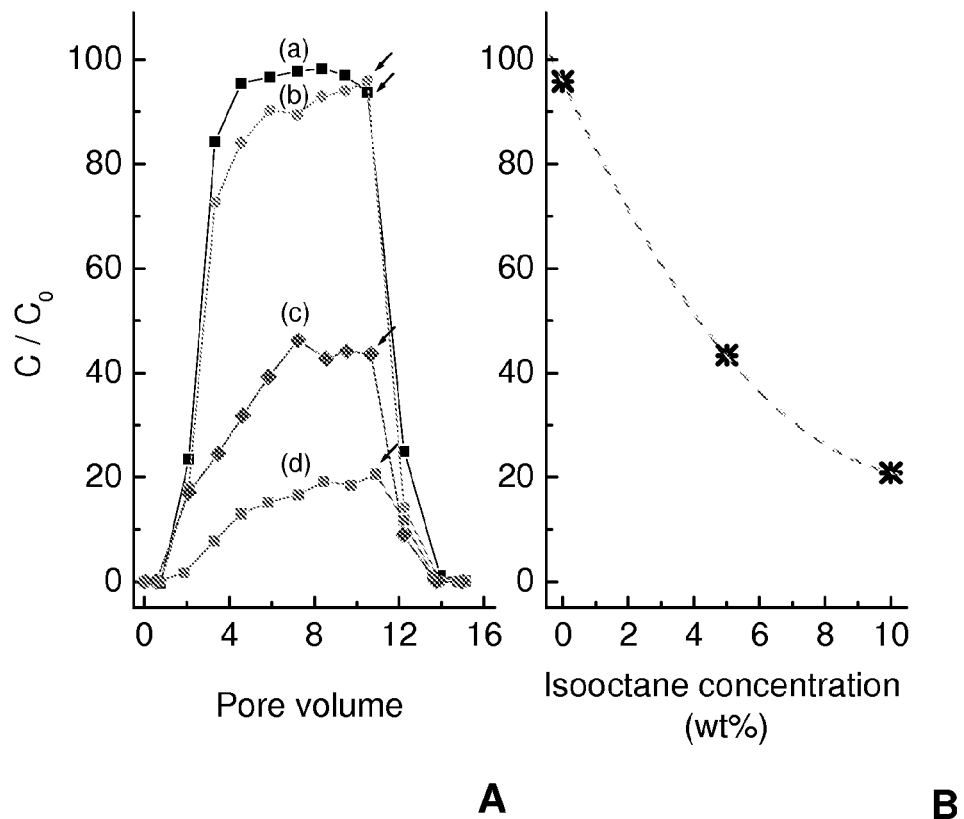

FIG. 9 provides additional breakthrough tests for PVA (50k)-fCBs, LsPVA(50k)-fCBs and HsPVA(50k)-fCBs. FIG. 9A provides breakthrough tests for components of nanoreporters in calcite-packed columns at 25° C. of LsPVA(50k)-fCB without isooctane or triheptylamine ("THA") (plot (a)); LsPVA(50k)-fCB associated with THA without isooctane ("THA/LsPVA(50k)-fCB") (plot (b)); THA/LsPVA(50k)-fCB with 5 wt % isooctane (plot (c)); and THA/LsPVA(50k)-fCB with 10 wt % isooctane (plot (d)). The $C/C_0$ value of the LsPVA(50k)-fCB was then determined by its UV absorbance at 232 nm, while the THA concentration was measured by electrospray mass spectrometry ("ESI-MS"). FIG. 9B is a graph showing the correlation between the $C/C_0$ value of THA and isooctane concentration in calcite columns.

Figure 10:
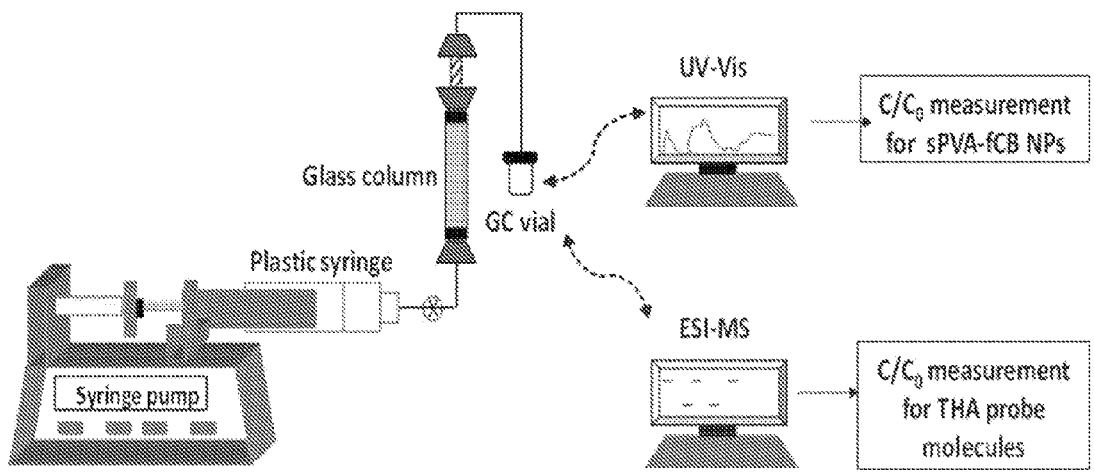

FIG. 10 provides a scheme of an apparatus for simulating the detection and quantitative analysis of hydrocarbon contents in downhole rocks. 20 ppm of THA/LsPVA-fCB in API brine was loaded into the plastic syringe and injected into a calcite-packed column with a given concentration of isooctane. The effluent was recovered and analyzed independently. The $C/C_0$ of LsPVA(50k)-fCB was measured by its UV absorbance at 232 nm. The THA was detected by ESI-MS by observing the protonated molecular ion (m/z=312.4).

Figure 11:
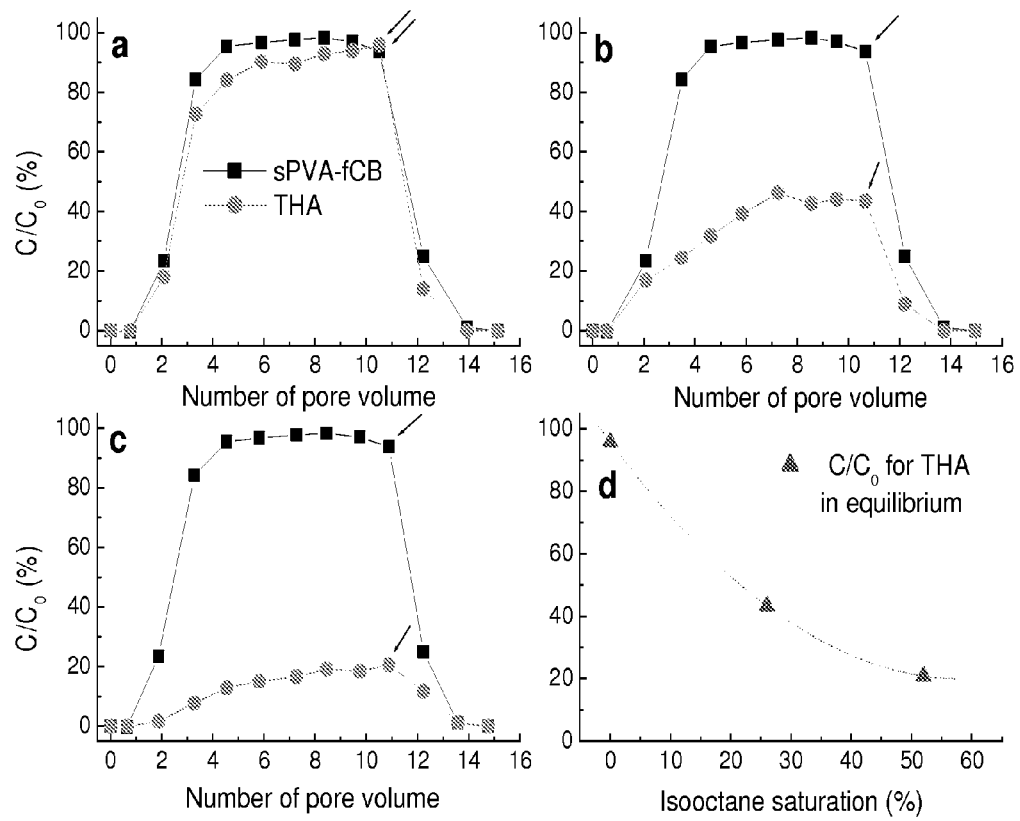

FIG. 11 provides additional breakthrough tests for THA/LsPVA(50k)-fCB nanoreporters in calcite-packed columns at 25° C. without isooctane (FIG. 11A), with 26% isooctane saturation (FIG. 11B), and with 52% isooctane saturation (FIG. 11C). The arrows indicate when the flow was switched from the THA/LsPVA-fCB solution to API brine. FIG. 11D shows the correlation between the $C/C_0$ value of THA and isooctane saturation in calcite columns.

Figure 12:
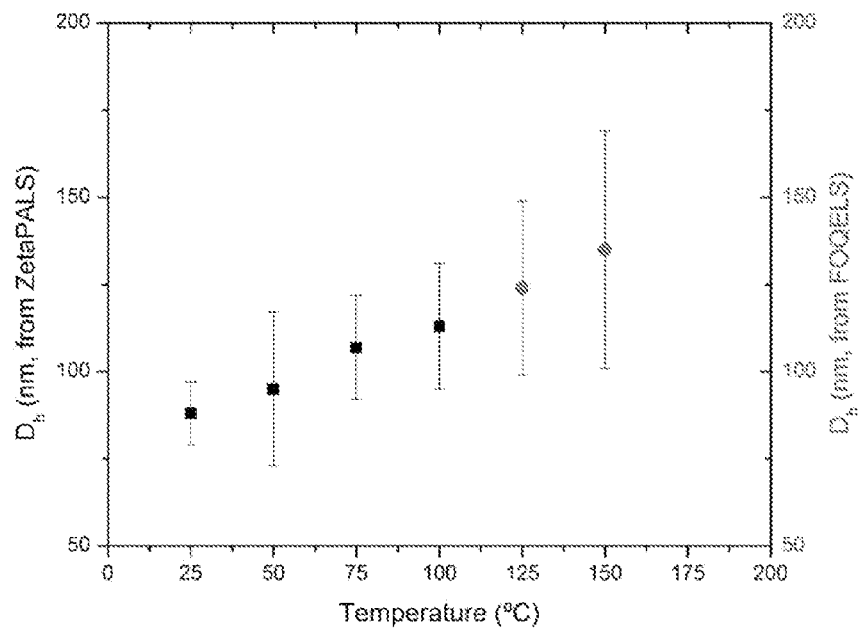

FIG. 12 provides DLS plots of oxidized carbon black ("OCB") lightly sulfated with PVA (50k) ("LsPVA(50k)-OCB") at different temperatures. The plots were measured by ZetaPALS and FOQELS in API brine. Hydrodynamic diameter ("$D_h$") is volume-based. The results show that the size of LsPVA(50k)-OCBs increases gradually with increased temperatures.

Figure 13:
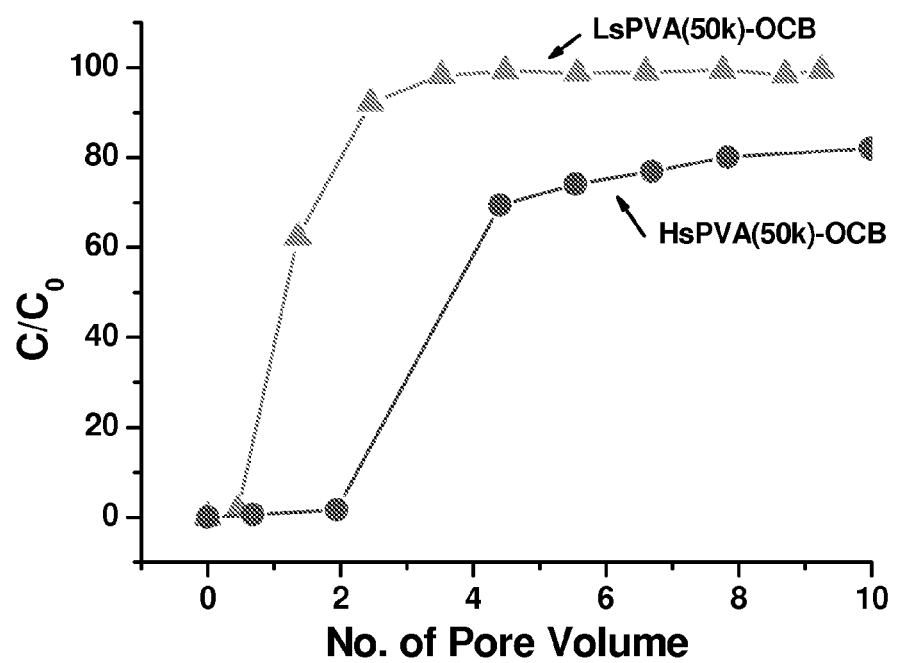

FIG. 13 shows the breakthrough studies of LsPVA(50k)-OCB and HsPVA(50k)-OCB in API brine in a sandstone column at 70° C. The concentration of nanocomposites was 20 mg/L, and the flow rate was 8 mL/hour (linear velocity 12.2 m/day). The results show that more than 95% of LsPVA (50k)-OCBs can flow through the sandstone column after 3 pore volumes. The results also show that about 80% of HsPVA-OCBs can flow through the column after 8 pore volumes.

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise. Parameters disclosed herein (e.g., temperature, time, concentrations, etc.) may be approximate.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

As energy demand continues to increase, it is desirable to produce as much oil as possible from existing and new oil wells. Tracers have been used to map entry and exit well correlations in the oil-field. However, many of the existing tracers do not provide any information about the environment between the entry and exit locations.

Oil production can be enhanced if the geology of oil fields can be accurately mapped out, and if flow from injection wells to production wells can be characterized. In particular, an approach is desired in which a sensor can be injected downhole, recovered at the production well, and analyzed for information about the subsurface. Though various sensors are available for such purposes, they have limited stability, durability, and breakthrough efficiency in geological structures.

For instance, in Applicants' previous work, the polyvinyl alcohol-modified oxidized carbon black ("PVA-OCB") demonstrated the best breakthrough efficiency and stability in seawater. However, such compositions had thermal stability limitations, such as being prone to agglomeration in seawater at higher temperatures (e.g., 70° C.). In addition, the compositions demonstrated limited breakthrough efficiency in certain charged porous media, such as dolomite and calcite rocks.

Therefore, it is desirable to design sensors that have enhanced stability, durability, and breakthrough efficiency in geological structures. In particular, sensors are desired that can simultaneously endure high temperature and high salinity while being transported through a variety of porous media. Various embodiments of the present disclosure address the foregoing.

In embodiments, the present disclosure pertains to systems and methods for detecting hydrocarbons in a geological structure by utilizing the nanocomposites of the present disclosure. As illustrated in FIG. 1A, systems and methods of the present disclosure can be performed by injecting the nanocomposites into the geological structure (step 10); collecting a sample of the nanocomposites after flow through the geological structure (step 12); determining the amount of the releasable probe molecules associated with nanocomposites in the collected sample (step 14); comparing the determined amount with the amount of releasable probe molecules associated with nanocomposites prior to injection into the geological structure (step 16); and correlating the compared amount to the presence of hydrocarbons in the geological structure (step 18), where a decrease in the amount of releasable probe molecules associated with nanocomposites in the collected sample is indicative of the presence of hydrocarbons in the geological structure.

FIG. 1B provides a scheme of an exemplary system and method of utilizing the nanocomposites of the present disclosure to detect hydrocarbons in a geological structure containing downhole rocks. In this example, the nanocomposites contain a carbon black core particle that is associated with sulfated polymer chains and a hydrophobic probe molecule that is releasable from the core particle upon exposure to hydrocarbons. The hydrophobic probe molecule serves as a probe during its downhole journey through the geological structure. If oil is present, then probe molecules are selectively released from the nanocomposites. Interrogation of the nanocomposites at the production site can then provide quantitative information regarding the oil content based upon the amount of hydrophobic probe molecules remaining on the nanoparticle.

As set forth in more detail herein, various nanocomposites may be utilized to detect hydrocarbons in various geological structures. In addition, various systems and methods may be utilized to detect the presence of hydrocarbons in geological structures.

Core Particles

Core particles generally refer to particles that can be transported through a geological structure. In some embodiments, it is desirable for the core particles to be stable to subsurface conditions. In some embodiments, it is also desirable for the core particles to endure various conditions in geological structures, such as high temperatures and salinities. In some embodiments, it is also desirable for the core particles to have mobility through different rocks in geological structures.

The nanocomposites of the present disclosure may include various types of core particles. In some embodiments, the core particles may include, without limitation, carbon black, functionalized carbon black, oxidized carbon black, carboxyl functionalized carbon black, carbon nanotubes, functionalized carbon nanotubes, graphenes, graphene oxides, graphene nanoribbons, graphene oxide nanoribbons, metal nanoparticles, silica nanoparticles, silicon nanoparticles, silicon oxide nanoparticles, silicon nanoparticles bearing a surface oxide, and combinations thereof. In some embodiments, the core particles may include functionalized carbon black ("fCB"), such as carboxyl-functionalized carbon black or oxidized carbon black.

In various embodiments, functionalized (e.g., oxidized) core particles may be prepared by reacting a dispersion of core particles with a mixture of fuming sulfuric acid and nitric acid. In some embodiments, oxidized carbon black may be prepared by a reaction of carbon black particles with an oxidizing agent, such as $KMnO_4$ in sulfuric acid or in a mixture of sulfuric acid and phosphoric acid. In some embodiments, the oxidized carbon black molecules may be highly oxidized and contain various oxidized functionalities, such as, for example, carboxylic acids, ketones, hydroxyl groups, and epoxides.

In some embodiments, the core particles of the present disclosure may be uncoated. In some embodiments, the core particles of the present disclosure may be coated with various coatings, such as polymers, surfactants, and combinations thereof.

The core particles of the present disclosure can have various sizes. For instance, in some embodiments, the core particles of the present disclosure can have diameters that range from about 1 nm to about 1 µm. In some embodiments, the core particles of the present disclosure can have diameters that range from about 1 nm to about 500 nm. In some embodiments, the core particles of the present disclosure can have diameters that are less than about 200 nm. In some embodiments, the core particles of the present disclosure can have diameters that are about 100 nm to about 200 nm. In some embodiments, the core particles of the present disclosure can have diameters that range from about 10 nm to about 50 nm.

The core particles of the present disclosure can also have various arrangements. For instance, in some embodiments, the core particles of the present disclosure may be individualized. In some embodiments, the core particles of the present disclosure may be in aggregates or clusters. In some embodiments, the core particles of the present disclosure may be in the form of clusters, where each cluster has about 3 to 5 core particles that are associated with one another.

The core particles of the present disclosure may also have various charges. For instance, in some embodiments, the core particles of the present disclosure may be positively charged. In some embodiments, the core particles of the present disclosure may be negatively charged. In some embodiments, the core particles of the present disclosure may be neutral. In some embodiments, the core particles of the present disclosure may include functionalized carbon blacks that are neutral in charge.

Polymers

The core particles of the present disclosure may be associated with various polymers. In some embodiments, the polymers may include, without limitation, amphiphilic polymers, hydrophobic polymers, hydrophilic polymers, and combinations thereof. In some embodiments, the core particles of the present disclosure may be associated with polymers through covalent bonds. In some embodiments, the core particles of the present disclosure may be associated with polymers through non-covalent bonds, such as ionic interactions, acid-base interactions, hydrogen bonding interactions, pi-stacking interactions, van der Waals interactions, adsorption, physisorption, self-assembly, sequestration, and combinations thereof.

In some embodiments, polymers may include, without limitation, poly(vinyl alcohol) ("PVA"), poly(ethylene glycol) ("PEG"), poly(propylene glycol) ("PPG"), poly(ethylene imine) ("PEI"), sorbitol, polysaccharides, polylactone, polyacrylonitrile ("PAN"), polyethylene ("PE"), poly(vinyl chloride) ("PVC"), poly(acrylic acid) ("PAA"), polystyrene ("PS"), high impact polystyrene ("HIPS"), polypropylene ("PP"), polyester, poly(hydroxyalkyl ester), poly(butadiene), vinyl polymers, step growth polymers, condensation polymers, and combinations thereof. In some embodiments, the core particles of the present disclosure may be associated with PVA. In some embodiments, the core particles of the present disclosure may be associated with PAA.

Sulfur-Based Moieties

In various embodiments, the polymers of the present disclosure may be associated with one or more sulfur-based moieties. Sulfur-based moieties generally refer to molecules with at least one sulfur atom. Without being bound by theory, the use of polymers with sulfur-based moieties can enhance the flow and penetration of nanocomposites into various geological structures.

In some embodiments, the sulfur-based moiety is a sulfate moiety with the following chemical formula: $-OSO_3R$. In some embodiments, R in the sulfate moiety may be at least one of H, Na, K, Li, $NH_4$, alkyl groups, aryl groups, phenyl groups, and combinations thereof. In some embodiments, the sulfur-based moiety is a sulfonate moiety with the following chemical formula: $-SO_3R$. In some embodiments, R in the sulfonate moiety may include at least one of H, Na, K, Li, $NH_4$, alkyl groups, aryl groups, phenyl groups, and combinations thereof.

In some embodiments, sulfur-based moieties may be covalently associated with polymers. In some embodiments, sulfur-based moieties may be non-covalently associated with polymers, such as through ionic interactions, acid-base interactions, hydrogen bonding interactions, pi-stacking interactions, van der Waals interactions, adsorption, physisorption, self-assembly, sequestration and combinations of such interactions.

In some embodiments, the polymer is a sulfated polyvinyl alcohol ("sPVA"), where one or more sulfate moieties are covalently linked to the polyvinyl alcohol. In some embodiments, the sulfated polyvinyl alcohol may be covalently linked to a core particle, such as a functionalized carbon black.

The sulfur-based moieties of the present disclosure may yield nanocomposites with various sulfur contents. For instance, in some embodiments, the nanocomposites of the present disclosure may have a sulfur content of less than about 2 atomic %. In some embodiments, the nanocomposites of the present disclosure may have a sulfur content from about 1 atomic % to about 1.5 atomic %. In some embodiments, the nanocomposites of the present disclosure may have a sulfur content of about 1.3 atomic %.

Releasable Probe Molecules

The core particles of the present disclosure may also be associated with one or more releasable probe molecules. Releasable probe molecules generally refer to probe molecules that are releasable from core particles upon exposure to hydrocarbons (e.g., oil, natural gas).

In some embodiments, the releasable probe molecules are non-covalently associated with core particles, such as through ionic interactions, acid-base interactions, hydrogen bonding interactions, pi-stacking interactions, van der Waals interactions, adsorption, physisorption, self-assembly, sequestration and combinations of such interactions. In some embodiments, the releasable probe molecules are covalently associated with core particles. In some embodiments, the releasable probe molecules are covalently associated with core particles through disulfide bonds or ester bonds. In some embodiments, the disulfide or ester bonds are cleavable upon exposure to hydrocarbons.

Various releasable probe molecules may be associated with the core particles of the present disclosure. In some embodiments, the releasable probe molecules may include at least one of fluorescent molecules, UV-active molecules, isotopically enriched molecules (e.g., molecules having mass spectra distinct form non-isotopically enriched molecules), radio-labeled molecules, radioactive molecules, metal nanoparticles, hydrophobic molecules, hydrophilic molecules, and combinations thereof.

In some embodiments, the releasable probe molecules are hydrophobic molecules. In some embodiments, the releasable probe molecules are hydrophobic molecules that are sequestered within hydrophobic regions of the core particles. In some embodiments, the releasable probe molecules are hydrophilic molecules that are sequestered within hydrophilic regions of the core particles.

In some embodiments, the releasable probe molecules include triheptylamine ("THA"). THA is a highly hydrophobic molecule due to its long alkyl chains. Furthermore, THA's nitrogen atoms can be easily distinguished by mass spectrometry according to the nitrogen rule, where an odd number of nitrogen atoms will afford an odd mass.

In some embodiments, releasable probe molecules may include fluorescent dyes, such as 1,5-diphenyloxazole or fluorescein. In some embodiments, the releasable probe molecules may be non-isotopically enriched molecules that are easily detectable by their mass spectra or other unique spectroscopic signature. In some embodiments, the releasable probe molecules may include metal nanoparticles and molecules that are sensitive to the presence of heavy metals (e.g., chelating ligands). In some embodiments, the releasable probe molecules are non-radioactive. In some embodiments, the releasable probe molecules are radioactive and thus detectable by a scintillation counter.

Hydrocarbon Detection

The nanocomposites of the present disclosure may be utilized to detect hydrocarbons in various geological structures. Such hydrocarbon detection techniques can also have various embodiments. In particular, various systems and methods may be utilized to inject nanocomposites into geological structures, collect nanoparticle samples after flow through the geological structures, and analyze the collected samples for the presence of hydrocarbons in the geological structures. Furthermore, embodiments of the present disclosure may be applied to various types of geological structures.

Geological Structures

Embodiments of the present disclosure may be applied to various geological structures. In some embodiments, the geological structures may include a downhole environment, such as an oil well or a subterranean or subsurface formation. In some embodiments, the geological structures of the present disclosure may be associated with various types of rocks, such as sandstone, dolomite, calcite, neutral formations, cationic formations, anionic formations, clays, shale, and combinations thereof.

In some embodiments, the geological structures pertaining to embodiments of the present disclosure may be penetrated by at least one vertical well. In some embodiments, the geological structures of the present disclosure may be penetrated by at least one horizontal well. In some embodiments, the geological structures of the present disclosure may be penetrated by at least one vertical well and at least one horizontal well.

The geological structures of the present disclosure may also be associated with various types of hydrocarbons. In some embodiments, the hydrocarbons may be associated with oil deposits. In some embodiments, the hydrocarbons may be derived from petroleum sources. Additional hydrocarbon sources can also be envisioned.

Nanoparticle Injection

Various systems and methods may also be utilized to inject nanocomposites into geological structures. In some embodiments, the injection may occur by pumping the nanocomposites into a geological structure. In some embodiments, the injection may occur by physically pouring the nanocomposites into a geological structure.

In some embodiments, the nanocomposites of the present disclosure may be dispersed in a fluid prior to injection into a geological structure. In some embodiments, the fluid may include at least one of water, brine, proppant, drilling mud, fracturing fluid, and combinations thereof. In some embodiments, the nanocomposites may be injected into a geological structure while dispersed in a substantially aqueous medium (i.e., >50% water). In other embodiments, the nanocomposites may be injected into a geological structure while dispersed in a substantially organic medium (i.e., >50% organic solvent).

In some embodiments, the nanocomposites may be injected into a geological structure while dispersed in an emulsion, such as an oil in water emulsion, where water is the continuous phase. In some embodiments, the nanocomposites may be injected into a geological structure while dispersed in an invert emulsion, such as a water in oil emulsion, where oil is the continuous phase.

Sample Collection

Various systems and methods may also be used to collect nanoparticle samples after flow through geological structures. In some embodiments, the nanocomposites of the present disclosure may be injected into a geological structure in a first location (e.g., an injection well) and recovered in a second location (e.g., a production well). In some embodiments, the nanocomposites of the present disclosure may be injected into a geological structure and recovered from the geological structure in the same location.

Detection of Hydrocarbons

Various systems and methods may also be used to detect hydrocarbons in geological structures. Such systems and methods generally include a determination of the amount of releasable probe molecules associated with nanocomposites in the collected sample, a comparison of the determined amount with the amount of releasable probe molecules associated with nanocomposites prior to injection, and a correlation of the compared amount to the presence of hydrocarbons in the geological structure. In general, a decrease in the amount of releasable probe molecules associated with nanocomposites in the collected sample corresponds to the presence of hydrocarbons in the geological structure.

Various systems and methods may be used to determine the amount of releasable probe molecules associated with nanocomposites. In some embodiments, the analysis may occur by mass spectrometry, such as electrospray mass spectrometry ("ESI-MS"). In some embodiments, the analysis may occur by spectroscopy, such as UV-vis spectroscopy. In some embodiments, the analysis may occur by fluorescence spectrometry. In some embodiments where the releasable probe molecule is radioactive, the detection may occur through detection of radioactivity using, for example, a scintillation counter.

Applications and Advantages

As set forth in more detail in the Examples herein, the nanocomposites of the present disclosure provide enhanced stability, durability, and breakthrough efficiency in various geological structures. For instance, the nanocomposites of the present disclosure can display effective flow through positively charged subsurface rocks, such as dolomite or calcite. Furthermore, the nanocomposites of the present disclosure can show tolerance against agglomerating under high temperature and high salinity conditions.

As such, the nanocomposites of the present disclosure can be used to more effectively detect the presence of hydrocarbons in various geological structures for numerous purposes. For instance, the nanocomposites of the present disclosure can be used in downhole oil detection, enhanced oil recovery, and environmental remediation of organic-contaminated land. In some embodiments, the nanocomposites of the present disclosure can be used to provide an effective assessment of stranded downhole oil content within various geological formations. In further embodiments, the nanocomposites of the present disclosure can provide a quantitative analysis of the hydrocarbon content in downhole rock formations associated with older oilfields. Additional applications can also be envisioned.

EMBODIMENTS

Reference will now be made to various embodiments of the present disclosure and experimental results that provide support for such embodiments. However, Applicants note that the disclosure herein is for illustrative purposes only and is not intended to limit the scope of the claimed subject matter in any way.

Example 1

Highly Stable Carbon Nanocomposites Designed for Downhole Hydrocarbon Detection

In this Example, Applicants demonstrate that sulfated polyvinyl alcohol functionalized carbon black, stable under high temperature and high salinity conditions, efficiently carries a hydrophobic compound through a variety of oil-field rock types and releases the compound when the rock contains hydrocarbons. In particular, Applicants show in this Example that nanocomposites possessing functionalized carbon black ("fCB") cores and sulfated polyvinyl alcohol ("sPVA") addends were designed to transport hydrocarbon detection molecules through subsurface rock formations. The sPVA-fCBs are stable under high-temperature and salinity conditions and are transported through a variety of oilfield rock types. A non-radioactive probe molecule that is easily detectable by mass spectrometry, triheptylamine ("THA"), was adsorbed onto the sPVA-fCBs. The THA was selectively released when the nanocomposites were passed through a column of isooctane-containing crushed rock, providing both entry and exit correlations and a measure of oil content.

In this Example, Applicants utilized a carboxyl group-functionalized carbon black ("fCB") as the core nanoparticle ("NP"). The fCB is less oxidized than the OCB core, resulting in a surface charge close to zero for fCB-containing nanocomposites in neutral aqueous solutions. Thus, the PVA-modified fCB exhibits improved performance when moving through charged rocks. Because ionic surfactants are not as temperature sensitive as non-ionic surfactants, the PVA-fCB nanocomposites were also sulfated to provide nanocomposites with slightly ionic properties. Sulfated PVA-fCB ("sPVA-fCB") nanocomposites used here show tolerance against agglomerating under high temperature and high salinity conditions. Furthermore, it is shown herein that sPVA-fCBs are capable of breaking through many subsurface rocks, such as sandstone, dolomite and calcite.

Example 1.1

Synthesis and Characterization of THA/sPVA-fCBs

In this Example, triheptylamine ("THA") was used as the probe molecule. The THA/sPVA-fCBs were found to efficiently transport THA through columns that simulate subsurface formations and selectively release the THA into hydrocarbon-containing rocks. Here, Applicants use the convention that "/" indicates a non-covalent attachment while "-" indicates a covalent attachment.

Since the CB lacks active groups on its surface, it is difficult to directly graft polymers onto its surface without any pretreatment. Hence, as illustrated in FIG. 2A, a radical initiator 4,4'-azobis(4-cyanopentanoic acid) ("ACPA") was used to introduce carboxyl groups onto the CB, forming carboxyl group-functionalized CB ("fCB"). The grafting of PVA onto the fCB surface was achieved by the condensation of hydroxyl groups of the PVA with carboxyl groups on the fCB using a N,N'-dicyclohexylcarbodiimide ("DCC") coupling reaction (FIG. 2B). Unbound PVA was removed after dialysis against running DI water. Thereafter, the PVA-grafted fCB ("PVA-fCB") was obtained.

For optimization, Applicants further changed the surface properties of the PVA-fCB nanocomposite by sulfation (FIG. 2C). Here, 3.0 mL of 1 M ClSO$_3$H was added to the as-synthesized PVA-fCB in DMSO. Next, the mixture was heated at 60° C. for 30 minutes to obtain lightly sulfated PVA-fCB ("LsPVA-fCB"). Highly sulfated PVA-fCB ("HsPVA-fCB") was prepared by adding 4.mL of 1 M ClSO$_3$H and heating for 60 minutes at 75° C.

FIG. 3 shows ATR-IR and XPS spectra for the PVA(50k)-fCB nanocomposites before and after sulfation. Besides certain vibrational bands in common, such as $v_{O-H}$ and $v_{C-H}$, the peaks at 1024 cm$^{-1}$, which are only found in the LsPVA(50k)-fCB and the HsPVA(50K)-fCB, could be attributed to S=O stretching from the sulfated PVA. The peak intensity then reflects the different extent of sulfation. The S2p XPS spectra of the LsPVA-fCB and the HsPVA-fCB provide further evidence that the HsPVA-fCB has almost twice the sulfur content of the LsPVA-fCB (2.2 atomic % vs. 1.3 atomic %, respectively, FIGS. 3E-F, insets).

Thermogravimetric analysis ("TGA") can be further used to provide evidence for PVA or sPVA on the fCB core. FIG. 4 shows typical TGA plots from LsPVA(50k)-fCBs, HsPVA(50k)-fCBs, and PVA(50k)-fCBs. Prior to running the TGA, the nanocomposites were heated at 120° C. to remove adsorbed water, and then cooled to 30° C. under argon. The sample was then heated to 800° C. at a rate of 3° C./minute. The TGA indicated that the weight loss of the PVA-fCB (94%) was slightly higher than the weight loss for oxidized carbon black ("OCB") functionalized with PVA ("PVA-OCB") (86%), as recorded in Applicants' previous reports. See, e.g., U.S. patent application Ser. No. 13/378,440 and PCT/US10/38363. Such findings indicate that the fCB cores are viable replacements for the OCB cores due to their high degrees of functionalization. The TGA weight loss of LsPVA-fCBs and HsPVA-fCBs was 78% and 81%, respectively.

Compared to the PVA-fCBs, both highly and lightly sulfated PVA-fCBs were expected to have larger weight loss due to the addition of sulfate groups. However, the TGA weight loss for the LsPVA-fCBs and HsPVA-fCBs was 78% and 81%, respectively. The PVA polymers were grafted onto the fCBs surface via ester bonds. From the chemical aspect, the sulfating agent, chlorosulfonic acid, not only sulfates the PVA, but it could also damage the ester bonds under strong base and acid condition. Without being bound by theory, Applicants believe that part of the grafted PVAs were lost during the sulfation process. After dialysis in running DI water, these unbound PVAs were therefore removed, causing the diminished PVA weight loss in the sPVA-fCBs. An alternative sulfation method that can be utilized is the commercial complex between pyridine and SO$_3$. See Example 1.12.

FIG. 5 shows scanning electron micrograph ("SEM") images of three different fCB-containing nanocomposites. 50,000 molecular weight PVA was coupled to the fCB to provide PVA(50k)-fCB nanocomposites with a particle size from 200 nm to 300 nm, as shown in FIG. 5A. These nanocomposites appear agglomerated because they were precipitated from acetone. Even so, each nanocomposite has the spherical shape of carbon black. After the PVA-fCB nanocomposite was lightly sulfated by ClSO$_3$H, the resulting LsPVA(50k)-fCB has a particle size distribution in a range between 100 nm and 200 nm. The HsPVA(50k)-fCB particles are almost twice as large (i.e., ~200 nm to ~400 nm) as the LsPVA(50k)-fCB. According to the zeta potential results, the HsPVA(50k)-fCB was measured to be ~-52 mV, which was much more negatively charged than LsPVA(50k)-fCB (~-10 mV) and PVA(50k)-fCB (~0 mV). These polyelectrolytes are made by negatively charged PVA due to the sulfation carrying a high net charge. The degree of expansion of the polyelectrolyte configuration increases as the degree of ionization increases due to Coulomb repulsion between the ionized groups. This explains why the particle size of the HsPVA-fCB nanocomposites is larger than that of PVA-fCB or LsPVA-fCB nanocomposites. Dynamic light scattering ("DLS") data of the nanocomposites in DI water at 25° C. also support the SEM results for particle size trends (see FIG. 6).

Example 1.2

Dispersion and Flow Characteristics of fCBs

API standard brine was used to disperse the fCB nanocomposites. API standard brine (pH 6.4) has much higher salinity than the synthetic seawater typically used to disperse oxidized carbon black NPs, thereby providing a more vigorous environment for maintaining dissolution. As FIG. 7A shows, when the temperature was elevated to 100° C., the PVA(50k)-fCB nanocomposites (that had been stable in synthetic seawater) quickly precipitated in the API brine at that temperature, and further could not be redispersed in the API standard brine solution upon cooling to room temperature. The LsPVA(50k)-fCB nanocomposites did not precipitate but was stable at 100° C. (FIG. 7B). However, the HsPVA(50k)-fCB was unstable in the API brine and formed a suspension (FIG. 7C), indicating that light sulfation produces the best results. The DLS data over a temperature range of 25° C. 70° C. (instrument limit) confirm the non-aggregation of the LsPVA(50k)-fCB (FIG. 6).

In order to evaluate the fCB-containing nanocomposites under more realistic conditions, transport of these nanocomposites through porous media that mimic natural rocks in oilfields was conducted. Sandstone and calcite, predominantly silica and calcium carbonate, which are often found in oil-rich environments, were ground and sieved to ~106-250 μm particles, then packed into a glass column. After each column was prepared, the volume of liquid contained in the fully saturated column (pore volume) was calculated. The breakthrough efficiency of the PVA-fCB nanocomposites was estimated by measuring the concentration of the PVA-fCB in the effluent (C) relative to the concentration in the influent (C$_0$) as a function of the amount of solution passed through the column measured in pore volumes ("PVs"). The API brine was used to evaluate the breakthrough performance the fCB nanocomposites.

FIG. 8 demonstrates the relative breakthrough efficiencies of three different fCB nanocomposites when they were passed through either sandstone- or calcite-packed columns at 70° C. The LsPVA(50k)-fCB nanocomposites in API brine showed breakthrough in both rock types in spite of the harsh environment. The breakthrough in the sandstone quickly reached greater than 95% at ~4 PV, while the breakthrough in the calcite initially approached only 85% at similar PV and then gradually increased to complete breakthrough.

Without being bound by theory, it is believed that the phenomenon that retards nanocomposite breakthrough in the calcite could be attributed to the bridging surface interactions between the LsPVA-fCB nanocomposites, the salts in brine solution and the calcite surface. The zeta potential of the LsPVA(50k)-fCB was -9.6 mV, while the HsPVA(50k)-fCB was -51.5 mV, providing a rationale for the fact that HsPVA(50k)-fCB nanocomposites blocked the column and had poorer transporting performance in both rocks (FIG. 8). Although the PVA(50k)-fCB nanocomposites had almost zero surface charge, the presence of highly concentrated salts in the API brine apparently causes the PVA-fCB to become unstable.

Compared to the fCB-based nanocomposites, the OCB surface (as described in U.S. patent application Ser. No. 13/378,440 and PCT/US10/38363) is highly negatively charged ($\xi$=–30.0 mV), probably due to the functionality introduced by the oxidative synthesis. In particular, OCBs can be made by treating carbon black with $KMnO_4$ in sulfuric or sulfuric and phosphoric acid mixtures, or treating carbon black with sulfuric and nitric acid mixtures (as described in U.S. patent application Ser. No. 13/378,440 and PCT/US10/38363). Thus, the OCBs bear many carboxylate groups, rendering the nanocomposites highly negatively charged.

Furthermore, the negatively charged surface of OCBs is apparently shielded by the grafted polymer ("PVA"), decreasing the zeta potential of the PVA(50k)-OCB to –0.6 mV, similar to that of the PVA(50K)-fCB. The sulfation then produced a negatively charged nanocomposite ($\xi$=–34.8 mV) for the HsPVA(50k)-OCB. Strong interactions between the HsPVA(50k)-OCBs, the electrolytes in the brine and the positively charged rocks retard the breakthrough efficiency of the sPVA(50k)-OCBs.

However, the fCBs as described in this Example are only sparsely carboxylated via a radical addition. Hence, the fCBs are nearly neutral, so they do not stick to positively charged formations, as shown here. And since neutral, they will also have little affinity to negatively charged or near-neutrally charged formations.

Example 1.3

Use of THA/LsPVA(50k)fCBs as Hydrocarbon Probes

Based on the testing data, LsPVA-fCBs are good nanoreporter candidates for hydrocarbon detection. In particular, their thermal stability and efficient mobility under harsh environments can allow them to effectively flow through various geological structures. Instead of the radioactive molecule PCB* (as described in U.S. patent application Ser. No. 13/378,440 and PCT/US10/38363), triheptylamine ("THA") was selected as a model compound for these hydrocarbon detection tests. The THA probe molecules could be adsorbed onto the LsPVA(50k)-fCB nanocomposites to yield the THA/LsPVA(50k)-fCB nanoreporter by mixing trace amount of THA (~5 µL) and 50 mL LsPVA(50k)-fCB aqueous solution. After stirring for one day, the resulting solution was passed through a size exclusive column (PD-10) in order to remove any unbound THA. The remaining THA was physisorbed onto the LsPVA(50k)-fCB hydrophobic domains, so that they would not be filtered out by the PD-10 column. A control experiment was done using a brine solution of THA without any LsPVA(50k)-fCB nanocomposites. The result showed low levels of THA after the PD-10 column filtration. Such results indicate that the fCB core is required for the efficient transport of probe molecules (such as THA) through the PD-10 column.

The THA/LsPVA(50k)-fCBs were subsequently flowed through a calcite column impregnated with a series of concentrations of isooctane from 0 to 10 wt % to simulate trapped oil in the formation. The LsPVA(50k)-fCBs had higher than 95% breakthrough at 25° C. (FIG. 9A, plot (a)). However, the THA adsorbed on the LsPVA(50K)-fCBs had different degrees of breakthrough that depended upon the isooctane concentration (FIG. 9A, plots (b)-(d)). The percentage of THA released to the isooctane phase correlated closely to the concentration of isooctane in the columns (FIG. 9B). Overall, these results indicate that LsPVA(50k)-fCBs efficiently transport the mass-tagged THA probe molecules through downhole porous media for hydrocarbon detection, despite higher temperature and salinity in most types of rocks. Furthermore, the more oil present in the downhole porous media, the more the THA molecules are removed from the nanocomposites.

For laboratory detection and quantitative analysis of the hydrocarbon content in downhole rocks, THA/LsPVA(50k)-fCBs were first diluted to ~20 ppm with the API brine. Next, the solution was pumped through a calcite-packed column by an automatic injection system (FIG. 10). The recovered solution was dual monitored by UV-vis (for polymer-fCB detection) and electrospray mass spectroscopy ("ESI-MS") (for THA detection). The LsPVA(50k)-fCB content in the effluent was measured by its UV absorbance at 232 nm, while the THA was detected by ESI-MS by observing the protonated molecular ion (m/z=312.4).

The THA/LsPVA(50k)-fCBs were subsequently pumped through a calcite column impregnated with isooctane from 0 to 52% saturation to simulate trapped oil in the formation. Oil saturation is a measurement of the degree of saturation of reservoir pore structure by reservoir oil. In this Example, oil saturation is a measure of the degree of column pore saturation by the isooctane. The 52% oil saturation corresponds to 10 wt % isooctane. Based on the results shown in FIG. 11, the pore volume breakthrough of the LsPVA(50k)-fCBs was independent of the isooctane oil saturation, showing over 95% breakthrough after 5 pore volumes (FIG. 11A). However, the amount of THA that was released from the THA/LsPVA(50K)-fCBs (FIGS. 11B-11C) depended directly on the isooctane oil saturation concentration in the column (FIG. 11D).

Example 1.4

Synthesis of Functionalized Carbon Black ("fCB")

4,4'-Azobis(4-cyanopentanoic acid) ("ACPA") was used for the introduction of carboxyl groups onto the carbon black surface. Typically, 3.0 g of carbon black and 6.0 g (21 mmol) of ACPA were added to 120 mL of tetrahydrofuran ("THF") (10.7 g, 148 mmol). The solution was stirred at 65° C. under nitrogen for 24 hours. The resulting mixture was filtered and the filter cake was washed with ~1 L THF. This was followed by drying at 100° C. in a vacuum oven (~100 Torr) for 24 hours to yield carboxyl group-functionalized carbon black (fCB, 2.9 g).

Example 1.5

Synthesis of Polyvinyl Alcohol Grafted fCB ("PVA-fCB")

The as-synthesized fCB (15 mg) was dispersed in a 100 mL round bottom flask with anhydrous DMSO (25 mL) by sonication (Cole-Parmer ultrasonic cleaner) overnight. The other flask containing polyvinyl alcohol (1.0 g, Mw ~50,000) and DMSO (25 mL, 27.5 g, 352 mmol) was heated to 70° C. until all the PVA was dissolved in the DMSO. When the PVA solution cooled down to room temperature, it was transferred to the original round bottom flask with fCB in DMSO. Next, N,N'-dicyclohexylcarbodiimide ("DCC", 140 mg, 0.68 mmol) and 4-dimethylaminopyridine ("DMAP", 20 mg, 0.16 mmol) were added. The reaction mixture kept stirring at room temperature for 24 hours. This was followed by transfer to a dialysis bag (MWCO=300 k). The mixture was then dialyzed in standing DMSO for 3 days. This was followed by dialysis in running DI water for 1 week to furnish a PVA-fCB aqueous solution (approximate 200 mL, 120 ppm).

Example 1.6

Synthesis of Sulfated Polyvinyl Alcohol Grafted fCB ("sPVA-fCB")

Before the second dialysis in running DI water, the resulting PVA-fCB in DMSO was further treated with 1 M $ClSO_3H/CH_3COOH$ (3.0 mL) at 60° C. for 30 min to yield lightly sulfated PVA-fCB ("LsPVA-fCB"). The highly sulfated PVA-fCB ("HsPVA-fCB") was obtained by treating 1 M $ClSO_3H/CH_3COOH$ (4.5 mL) at 75° C. for 90 minutes. After sulfation, the resulting solution was neutralized to ~7.0 with 1M NaOH(aq) until the pH reached ~7.0. The LsPVA-fCB or HsPVA-fCB aqueous solution was obtained after dialysis (MWCO=300k) under running DI water for another 1 week (final solution: approximately 200 mL, 120 ppm).

Example 1.7

Preparation of THA/LsPVA-fCB Nanoreporter

Here, 50 mL of the LsPVA-fCB solution was stirred with a trace amount of THA (~5 μL, 4 mg, 0.013 mmol) for one day. The solution was then passed through a size exclusive column (PD-10) in order to remove any unbound THA. The remaining THA was physisorbed onto the LsPVA-fCB hydrophobic domains, so that they would not be filtered out by the PD-10 column.

Example 1.8

Preparation of API Brine $CaCl_2.2H_2O$ and NaCl were added to deionized water to prepare a solution with the following concentrations: $CaCl_2$ (2%, w/w) and NaCl (8%, w/w).

Example 1.9

General Column Preparation

Ground rock grains were slowly packed into the glass column with a length of about 67 cm (Omnifit borosilicate glass columns with an adjustable end piece, cross sectional area=0.34 $cm^2$, Bio-Chem Valve Inc., Boonton, N.J.). The packed rock materials were retained by 10 μm stainless steel screens (Valco Instruments Inc., Houston, Tex.) on both sides of the column. A three-way valve was used to connect a 60 mL plastic syringe and the column. The whole system was connected by PTFE tubing (Omnifit). The packed columns were flush with $CO_2$ (purity >99%) for 30 minutes to remove the trapped air bubbles. Next, the columns were flushed with API brine at a flow rate of 8 mL/hour for 24 hours to stabilize rock grains. Tritiated water, as a non-reactive tracer, was injected into the columns to characterize the porosity and dispersity of the column. The pH of influent solutions in all column experiments was 6.4. The column properties are summarized in Table 1.

TABLE 1

|  | Flow rate (m/24 h) | Dispersion Coefficient ($cm^2$/min)[a] | Porosity | $R^2$ |
|---|---|---|---|---|
| Sandstone | 9.3 | 0.0245(0.0026) | 0.4795(0.0017) | 0.998 |
| Calcite | 9.3 | 0.0416(0.0032) | 0.4500(0.0016) | 0.998 |

[a]Numbers in parentheses are the standard deviations

Example 1.10

Nanomaterial Sample Breakthrough

The nanocomposites were suspended in the API brine and filtered through a PES filter of 0.45 μm pore size (Whatman, USA). The nanocomposites suspension was then pumped (New Era Pump System Inc., Wantagh, N.Y.) through the columns at a linear average velocity of 9.3 m/day. The effluent was collected in a 2 mL glass vial. The concentration of nanocomposites was measured by UV-visible spectrophotometer (DR/4000, HACH Company, Loveland, Colo.) at 232 nm. When the breakthrough reached a plateau, the column was flushed with API brine.

Example 1.11

Oil-Containing Column Preparation

After being flushed with API brine for 24 hours, the calcite column was then flooded with isooctane (Fisher Scientific, USA) at a flow rate of 6 mL/hour until no water was produced. Next, API brine was injected into the column at 8 mL/hour until no more oil was produced. The volume of oil injected into the column was calculated by measuring the amount of oil produced from the water flood. Residual oil saturation is the ratio of the volume of isooctane to the predetermined pore volume.

Example 1.12

Synthesis of sPVA-fCBs by Use of Pyridine-$SO_3$ 50 mg of fCB (15 nm) and 50 mL of anhydrous DMSO (0.7 mol) were dissolved in a dry 100 mL round bottom flask fixed with a stir bar. The solution was then bath-sonicated for 3 hours. Next, 500 mg of PVA (50 k) (0.01 mmol) was added to the solution and heated at 80° C. for 0.5 hours to dissolve the PVA (50 k). After cool down, about 200 mg (0.97 mmol) of DCC and 20 mg (0.10 mmol) of DMAP were added. The solution was then stirred for 12 hours at room temperature. After heating the solution to 65° C., 362 mg (2.27 mmol) of sulfur trioxide pyridine complex was added. The solution was then stirred for 3 hours before being neutralized by 1 M NaOH (~2 mL). Next, the solution was transferred to a dialysis bag (MWCO=50 k) and dialyzed against running DI water for 1 week. Next, the solution in the dialysis bag was filtered through a 0.22 μm filter unit.

Example 1.13

Preparation of sPVA-OCB by Use of Pyridine-$SO_3$

In this example, sulfated PVA-grafted OCB ("sPVA-OCB") was synthesized by using sulfur trioxide pyridine complex as the sulfation reagent. First, OCB was prepared, as previously described. See Berlin et al., *Energy Environ. Sci.*, 2011 (4): 505-509. Briefly, a mixture of sulfuric acid (98%, 180 mL, 3.3 mol) and phosphoric acid (85.8%, 20 mL, 0.34 mol) was added to carbon black ("CB", 15 nm, 1 g). Next, the mixture was stirred. Potassium permanganate (6 g, 38 mmol) was added in 3 portions over 15 minutes to the reaction mixture. After 15 minutes, the mixture was heated to 58° C. and stirred at that temperature for 1 hour. The reaction mixture was cooled to room temperature and poured onto ice containing 10 mL of hydrogen peroxide (30%). Sodium hydroxide (~300 g, 7.62 mol) was slowly added as a fine powder into the acidic reaction mixture until the OCB precipitated out as a black solid. The OCB was collected by centrifuging at 4100 r.p.m. for 90 minutes. After the solution was decanted, the resulting wet OCB was re-dispersed in 150 mL of 10% hydrochloric acid and centrifuged again. This process was repeated twice more. Then the wet OCB was dispersed in 50 mL DI water and transferred to a dialysis bag (MWCO=2000) and dialyzed in running DI water for 1 week to remove the residual acid and inorganic salts. The water was removed under reduced pressure and the damp OCB was dried in a vacuum oven (~100 Torr) at 70° C. for 16 hours to provide OCB (0.51 g).

Next, the OCB was used to prepare both LsPVA(50k)-OCB and HsPVA(50k)-OCB. This was done by adding 50 mg of OCB (15 nm) and 50 mL (0.7 mol) of anhydrous DMSO to a dry 100 mL round bottom flask containing a stir bar. The solution was bath sonicated for 3 hours. Next, 500 mg (0.01 mmol) of PVA (50 k) was added to the solution. This was followed by heating at 80° C. for 0.5 hours to dissolve PVA (50 k). The solution was then cooled down. Thereafter, 200 mg (0.97 mmol) of DCC and 20 mg (0.10 mmol) of DMAP were added to the solution. The solution was then stirred for 12 hours at room temperature. The solution was then heated to 65° C. Next, 362 mg (2.27 mmol) of sulfur trioxide pyridine complex was added to the solution. The solution was stirred for 3 hours before being neutralized (pH=7 monitored by pH meter) by 1 M NaOH (~2 mL). The solution was then transferred to a dialysis bag (MWCO=50 k) and dialyzed against running DI-water for 1 week. Next, the solution in the dialysis bag was filtered through a 0.22 μm filter unit. 200 mL (220 ppm) of LsPVA(50k)-OCB solution was obtained.

To prepare HsPVA(50k)-OCB, the adding amount of sulfur trioxide pyridine complex was increased to 724 mg (4.54 mmol). In addition, the amount of 1 M NaOH was increased to about 4 mL. The other steps remained the same.

Example 1.14

Characterization of sPVA-OCBs

To characterize the formed sPVA-OCBs, DLS was done at 25° C., 50° C., 75° C., 100° C., 125° C. and 150° C. in API brine. As illustrated in FIG. 12, the particle size of the LsPVA (50k)-OCB shows a gradual increase depending upon increased temperatures. In addition, the zeta potentials of LsPVA(50k)-OCB and HsPVA(50k)-OCB are −9.5 mV and −20.1 mV in DI water at room temperature, respectively.

The breakthrough studies of sPVA-OCB were carried out in sandstone column at 70° C. The concentration of nanocomposites was 20 mg/L and the Flow rate was 8 mL/hour (linear velocity 12.2 m/day). As shown in FIG. 13, LsPVA(50k)-OCB reaches the highest breakthrough efficiency (more than 95%) after 3 pore volumes. However, HsPVA-OCB reaches the highest value (about 80%) after 8 pore volumes.

With respect to embodiments of the present invention, Applicants have developed PVA-fCB nanocomposites that remain stable at high temperatures by choosing appropriately sized (molecular weight) PVA for functionalization and sulfating a small portion of the PVA hydroxyl units. The OCB core was replaced by the fCB composite core without changing its intrinsic properties. After sulfation, the sPVA-fCB nanocomposites exhibited stability at the high temperature and high salinity conditions expected in the downhole rock environment. The sPVA-fCB nanocomposites efficiently transported mass-tagged probe molecules through a variety of oil field rock types and selectively released the probe molecules into hydrocarbon-containing rocks. Based on the recovery of nanoreporters, one can quantitatively analyze the stranded downhole oil content. This can be applied to downhole embodiments for determining the amount of oil downhole.

The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of approximately 1 to approximately 4.5 should be interpreted to include not only the explicitly recited limits of 1 to approximately 4.5, but also to include individual numerals such as 2, 3, 4, and sub-ranges such as 1 to 3, 2 to 4, etc. The same principle applies to ranges reciting only one numerical value, such as "less than approximately 4.5," which should be interpreted to include all of the above-recited values and ranges. Further, such an interpretation should apply regardless of the breadth of the range or the characteristic being described. Any steps recited in any method or process claims may be executed in any order and are not limited to the order presented in the claims.

What is claimed is:

1. A nanocomposite suitable for detecting hydrocarbons in a geological structure, wherein the nanocomposite comprises:
   a core particle;
   a polymer associated with the core particle;
   a sulfur-based moiety associated with the polymer; and
   a releasable probe molecule associated with the core particle,
   wherein the releasable probe molecule is releasable from the core particle upon exposure to hydrocarbons,
   wherein the releasable probe molecule is triheptylamine ("THA").

2. The nanocomposite of claim 1, wherein the core particle is selected from the group consisting of carbon black, functionalized carbon black, oxidized carbon black, carboxyl functionalized carbon black, carbon nanotubes, functionalized carbon nanotubes, graphenes, graphene oxides, graphene nanoribbons, graphene oxide nanoribbons, metal nanoparticles, silica nanoparticles, silicon nanoparticles, silicon oxide nanoparticles, silicon nanoparticles bearing a surface oxide, and combinations thereof.

3. The nanocomposite of claim 1, wherein the sulfur-based moiety is a sulfate moiety with the following chemical formula:

wherein R is selected from the group consisting of H, Na, K, Li, NH$_4$, alkyl groups, aryl groups, phenyl groups, and combinations thereof.

4. The nanocomposite of claim 1, wherein the sulfur-based moiety is a sulfonate moiety with the following chemical formula:

—SO$_3$R, wherein R is selected from the group consisting of H, Na, K, Li, NH$_4$, alkyl groups, aryl groups, phenyl groups, and combinations thereof.

5. The nanocomposite of claim 1, wherein the nanocomposite has a neutral charge.

6. A method for detecting hydrocarbons in a geological structure, wherein the method comprises:
 injecting nanocomposites into the geological structure, wherein the nanocomposites each comprise:
  a core particle,
  a polymer associated with the core particle,
  a sulfur-based moiety associated with the polymer, and
  a releasable probe molecule associated with the core particle, wherein the releasable probe molecule releases from the core particle upon exposure to hydrocarbons within the geological structure, wherein the releasable probe molecule comprises tri-heptylamine ("THA");
 collecting a sample of the nanocomposites after flow through the geological structure;
 determining an amount of the releasable probe molecules associated with the nanocomposites in the collected sample;
 comparing the determined amount with an amount of releasable probe molecules associated with the nanocomposites prior to injection into the geological structure; and
 correlating the compared amount to presence of hydrocarbons in the geological structure, wherein a decrease in the amount of releasable probe molecules associated with nanocomposites in the collected sample relative to the amount of the releasable probe molecules associated with the nanocomposites prior to injection into the geological structure is indicative of the presence of hydrocarbons in the geological structure.

7. The method of claim 6, wherein the releasable probe molecule is non-covalently associated with the core particle.

8. The method of claim 6, wherein the releasable probe molecule is hydrophobic.

9. The method of claim 6, wherein the releasable probe molecule is non-radioactive.

10. The method of claim 6, wherein the polymer is poly(vinyl alcohol) (PVA).

11. The method of claim 6, wherein the sulfur-based moiety is a sulfate moiety with the following chemical formula:

—OSO$_3$R, wherein R is selected from the group consisting of H, Na, K, Li, NH$_4$, alkyl groups, aryl groups, phenyl groups, and combinations thereof.

12. The method of claim 6, wherein the sulfur-based moiety is a sulfonate moiety with the following chemical formula:

—SO$_3$R, wherein R is selected from the group consisting of H, Na, K, Li, NH$_4$, alkyl groups, aryl groups, phenyl groups, and combinations thereof.

13. The method of claim 6, wherein:
 the polymer is sulfated or sulfonated polyvinyl alcohol,
 the core particle is functionalized carbon black, and
 the sulfated or sulfonated polyvinyl alcohol is covalently associated with the functionalized carbon black.

14. The method of claim 6, wherein the determining of the amount of releasable probe molecules associated with nanocomposites in the collected sample is determined by mass spectrometry.

15. The method of claim 6, wherein the nanocomposites have a neutral charge.

16. A system for detecting hydrocarbons in a geological structure, wherein the system comprises:
 nanocomposites to be injected into the geological structure in combination with measurement equipment configured to determine an amount of releasable probe molecules associated with the nanocomposites, wherein the nanocomposites each comprise:
  a core particle,
  a polymer associated with the core particle,
  a sulfur-based moiety associated with the polymer, and
  a releasable probe molecule associated with the core particle, wherein the releasable probe molecule configured to release from the core particle upon exposure to hydrocarbons within the geological structure, wherein the releasable probe molecule comprises tri-heptylamine ("THA");
 equipment configured to inject the nanocomposites into the geological structure;
 equipment configured to recover a sample of the nanocomposites after flow through the geological structure;
 measurement equipment configured to determine an amount of the releasable probe molecules associated with the nanocomposites in the collected sample;
 comparing the determined amount with an amount of releasable probe molecules associated with the nanocomposites prior to injection into the geological structure; and
 equipment configured to correlate the compared amount to presence of hydrocarbons in the geological structure, wherein a decrease in the amount of releasable probe molecules associated with nanocomposites in the collected sample relative to the amount of the releasable probe molecules associated with the nanocomposites prior to injection into the geological structure is indicative of the presence of hydrocarbons in the geological structure.

17. The system of claim 16, wherein the sulfur-based moiety is a sulfate moiety with the following chemical formula:

—OSO$_3$R, wherein R is selected from the group consisting of H, Na, K, Li, NH$_4$, alkyl groups, aryl groups, phenyl groups, and combinations thereof.

18. The system of claim 16, wherein the sulfur-based moiety is a sulfonate moiety with the following chemical formula:

—SO$_3$R, wherein R is selected from the group consisting of H, Na, K, Li, NH$_4$, alkyl groups, aryl groups, phenyl groups, and combinations thereof.

19. The system of claim 16, wherein:
 the polymer is sulfated or sulfonated polyvinyl alcohol,
 the core particle is functionalized carbon black, and
 the sulfated or sulfonated polyvinyl alcohol is covalently associated with the functionalized carbon black.

20. The system of claim 16, wherein the measurement equipment configured to determine the amount of releasable probe molecules associated with nanocomposites comprises a mass spectrometer.

* * * * *